US012569348B2

(12) United States Patent
Kang et al.

(10) Patent No.: US 12,569,348 B2
(45) Date of Patent: Mar. 10, 2026

(54) BEARING COMPONENT FOR ARTIFICIAL KNEE JOINT

(71) Applicants: TJC life Co., Ltd., Seoul (KR); Kyoung Tak Kang, Seoul (KR); Ji Hoon Nam, Seoul (KR)

(72) Inventors: Kyoung Tak Kang, Seoul (KR); Ji Hoon Nam, Seoul (KR); Yong Gon Koh, Seoul (KR)

(73) Assignees: TJC life Co., Lyd., Seoul (KR); Kyoung Tak Kang, Seoul (KR); Ji Hoon Nam, Seoul (KR)

( * ) Notice: Subject to any disclaimer, the term of this patent is extended or adjusted under 35 U.S.C. 154(b) by 624 days.

(21) Appl. No.: 17/568,153

(22) Filed: Jan. 4, 2022

(65) Prior Publication Data

US 2022/0249240 A1      Aug. 11, 2022

(30) Foreign Application Priority Data

Feb. 10, 2021      (KR) ......................... 10-2021-0019434

(51) Int. Cl.
*A61F 2/38*          (2006.01)
*A61F 2/30*          (2006.01)
(52) U.S. Cl.
CPC ........ *A61F 2/3868* (2013.01); *A61F 2/30771* (2013.01); *A61F 2/3859* (2013.01); *A61F 2002/30125* (2013.01); *A61F 2002/30158* (2013.01); *A61F 2002/30164* (2013.01); *A61F 2002/30878* (2013.01)

(58) Field of Classification Search
None
See application file for complete search history.

(56) References Cited

U.S. PATENT DOCUMENTS 5,344,460 A * 9/1994 Turanyi .................. A61F 2/389
                                                                     623/20.33
9,204,967 B2 * 12/2015 Wyss ........................ A61F 2/38
(Continued)

FOREIGN PATENT DOCUMENTS

EP          0 724 868 A1      8/1996
EP          3335674 A2        6/2018
JP          2011-092737 A     5/2011
(Continued)

*Primary Examiner* — Melanie R Tyson
*Assistant Examiner* — Melissa A Hoban
(74) *Attorney, Agent, or Firm* — You & IP, LLC

(57)          ABSTRACT

Proposed is a bearing component for an artificial knee joint, the bearing component including a body part, whose plane shape is oval, having an indentation portion formed by depressing a posterior center to a predetermined depth toward a center of the body part, a protruding portion protruding from an upper surface of the body part and introduced into an opening of a femoral component, a coupling portion provided on a lower surface of the body part, and having an engagement surface of a certain height to form a step difference with an outer circumferential surface of the body part, the engagement surface being formed on left and right sides of the coupling portion, and being not formed on an indentation surface, and a fastening portion having a plurality of coupling protrusions formed in a portion where the engagement surface of the coupling portion is not formed.

16 Claims, 11 Drawing Sheets

(56)                    References Cited

U.S. PATENT DOCUMENTS

2014/0277535  A1      9/2014  Metzger et al.
2018/0271666  A1*     9/2018  Lenz ...................... A61F 2/389

FOREIGN PATENT DOCUMENTS

| | | | |
|---|---|---|---|
| JP | 2015513966 | A | 5/2015 |
| KR | 10-2012-0102576 | A | 9/2012 |
| KR | 10-2012-0112816 | A | 10/2012 |
| KR | 10-1769125 | B1 | 8/2017 |

* cited by examiner

<before surgery>  <after surgery>

BEARING COMPONENT FOR ARTIFICIAL KNEE JOINT

CROSS REFERENCE TO RELATED APPLICATION

The present application claims priority to Korean Patent Application No. 10-2021-0019434, filed Feb. 10, 2021, the entire content of which is incorporated herein for all purposes by this reference.

BACKGROUND OF THE INVENTION

1. Field of the Invention

The present disclosure relates to a bearing component for an artificial knee joint and, more particularly, to a bearing component that can be easily combined or separated with small force by coupling protrusions that are coupled with the outer perimeter of the dovetail-shaped protruding surface of a tibial component, and an artificial knee joint including the same.

2. Description of Related Art

The knee joint is a joint made up of three bones surrounding the knee (the femur, the tibia, and the patella), and cartilage. The knee joint is a component of the human body that allows for extension and flexion of the knee, and together with the hip joint (coxa), the knee joint is said to be the most essential joint that enables humans to walk upright.

The bones forming the main knee joint meet at the bottom of the femur, the top of the tibia, and the back of the patella (kneecap), allowing the leg to bend backwards at the knee.

Patients with reduced or lost knee joint function due to abrasion of knee joint parts, bone tissue aging, or an accident, etc., require orthopedic surgery, and as we have entered a homo-hundred era, the importance of procedures for osteoarthritis patients and the number of patients are increasing day by day.

Recently, knee joint replacement, also known as knee arthroplasty, is widely performed for patients who cannot recover through life-style improvement, conservative treatment such as drug treatment and physical therapy, or arthroscopic surgery or cartilage regeneration to respond to mid-term symptoms due to serious damage to the joint area, and artificial components made of materials such as metal, ceramic, or polyethylene are used for the joint movements of the artificial knee.

In general, there are three components constituting the artificial knee: a femoral component coupled to the distal end of the femur, tibial component coupled to the proximal end of the tibia, and bearing component (replacing cartilage) positioned between those two components.

FIG. 1A is a view showing a knee of a patient before and after a knee replacement surgery is performed, and FIG. 1B is a view showing an artificial knee joint 10 according to the conventional art.

The artificial knee joint 10 is composed of a metal, ceramic, or resin tibial component 13 that is directly fixed to the tibia and a resin bearing component 12 that is fixed or attached to the upper surface of the tibial component 13 to be movable and comes into contact with the femoral component 11. The bearing component 12 shown in FIG. 1 is fixed to the tibial component 13 and thus can be classified as a fixed bearing type.

Here, as a locking mechanism for fixing the bearing component 12 to the tibial component 13, a hook type, a pin type, or a dovetail type is applied.

The mechanism for fixing the bearing component and the tibial component in a hook type features: hooks whose shapes are opposed to each other formed at the front (in the ventral direction of the body, anterior) and the rear (the dorsal direction of the body, posterior) of the upper surface of the tibial component; and grooved portions to be fitted into the hooks formed on an engagement surface of the bearing component coupled to the upper surface of the tibial component.

The hook type is easy to fasten, but when you want to take out the front hook part when the front and rear hooks are combined, the front hook is hooked and it is very difficult to pull out. Poor stability after fastening of the rear hook side in the combined state is also problematic.

Next, the pin type is similar to the hook type in that hooks are formed at the front and rear ends of the upper surface of the tibial component, and a groove into which the hooks are fitted are formed at the rear of the engagement surface of the bearing component coupled to the upper surface of the tibial component, but it is different in that, as shown in FIG. 2, the hooks 13-1 formed at the front end of the upper surface of the tibial component have grooved portions formed on the front sides and a separate pin 13-2 that performs as a latch is used to engage the tibia component when a hook 12-1 formed in the front of the engagement surface of the bearing component is seated.

The pin type has the advantage of being easier to remove the bearing component compared to the hook type since it is a method of separating the bearing component after pulling out the pin. However, like the hook type, there is a problem of poor stability after fastening and it is difficult to separate the bearing component during reoperation because an additional pin inserted in the lateral direction is required.

Finally, the dovetail type having a configuration as shown in FIG. 3, has a structure in which a dovetail-shaped fastening part 12-3 formed to a predetermined depth on an engagement surface 12-7 of the bearing component 12 is fitted into a dovetail-shaped accommodating part 13-3 that is formed to protrude at a predetermined height from the upper surface 13-7 of the tibial component 13, and in which the bearing component is engaged with and inserted into the tibial component by sliding it from anterior to posterior on the top surface 13-7 of the tibial component as shown in FIG. 4.

The dovetail type has better stability after fastening compared to the hook type or pin type discussed earlier and has the advantage of easy separation by inserting a tool into a separation groove 12-6, but there is a problem in that excessive force is required during fastening.

That is, as shown in FIG. 4C, the engagement surface of the bearing component comes into contact with an outer perimeter ridge (13-5, configured to restrict the forward movement of the bearing component in the engaged state) formed in the front of the tibial component in the process in which an engaging groove of the dovetail-shaped fastening part 12-3 of the bearing component 12 is fitted into an engaging groove of the dovetail-shaped accommodating part 13-3 of the tibial component 13, and because of this, the bearing component should be inserted into the tibial component in surface contact until a grooved portion 12-4 formed on an rear outer perimeter of the dovetail-shaped fastening part 12-3 of the bearing component 12 corresponds to a ridge 13-4 formed on the rear outer perimeter of the dovetail-shaped accommodating part 13-3 of the tibial component 13, and thus excessive force is required during the insertion process. In the actual surgical procedure, an impactor 14 as shown in FIG. 4D or FIG. 5A or a trigger-type dedicated tool 15 or hammer as shown in FIG. 5B is needed to apply a large force.

There are other problems with using these tools: when striking with an impactor or hammer, the impact may cause cracks in a patient's bones; and a trigger-type tool requires a large grip force to operate, causing inconvenience to an operator, and the cost increases because the tool must be specially crafted.

Meanwhile, after knee replacement, revision surgery is sometimes required due to various causes such as damage or detachment of the implant, or infection, but revision surgery is more difficult than the initial operation since it is performed in a more advanced state of the bone defect and the procedure is also complicated, making it difficult to stably install a new implant.

In addition, when a large force is applied, such as artificially widening the gap in the process of separating the previously inserted artificial knee by using assistive devices, etc. to separate the closely coupled bearing component 12 and the tibial component 13, the risk associated with reoperation increases.

Documents of Related Art (Patent Document 1) Korean Patent Registration Notification No. 10-1769125 (registered Aug. 10, 2017)

SUMMARY OF THE INVENTION

Accordingly, the present disclosure has been made keeping in mind the above problems occurring in the related art with respect to the hook type, pin type, or dovetail type locking mechanisms for fixing the bearing component 12 to the tibial component, such as stability after fastening, separation during reoperation, and application of excessive force during fastening, and the present disclosure is intended to provide a bearing component and an artificial knee joint including the same that maximizes the advantages of the dovetail type with high stability after fastening, while increasing the ease of work during fastening, improving stability after fastening, and making it easier to separate by reducing the excessive force required for fastening and disengaging in the conventional dovetail type structure.

In order to achieve the above objective, according to one embodiment of the present disclosure, there is provided a bearing component 200 for an artificial knee joint including a body part 210, whose plane shape is oval as a whole, having an indentation portion 211 formed by depressing a posterior center of the body part to a predetermined depth toward a center of the body part 210, a protruding portion 220 formed on an upper surface of the body part 210 and introduced into an opening of a femoral component, a coupling portion 230 provided on a lower surface of the body part 210, and having an engagement surface 231 of a certain height to form a step difference with an outer circumferential surface of the body part, the engagement surface 231 being formed on the left and right sides of the coupling portion in a shape in which the shape of the body part is reduced by a predetermined ratio, and being not formed on an indentation surface up to a certain distance forward from the indentation portion 211 of the body part, and a fastening portion 240 in which a plurality of coupling protrusions 250 are formed near the center of the body part in a portion where the engagement surface 231 of the coupling portion 230 is not formed.

The bearing component 200 for an artificial knee joint is made of at least one selected from the group consisting of a composite material comprising at least one from the group consisting of UHMWPE, PEEK, carbon fiber reinforced polymer or glass fiber reinforced polymer, and polyethylene (PE). Here, XLPE or HXLPE may be used as the UHMWPE, and the UHMWPE may further comprise vitamin E.

The plurality of coupling protrusions 250 formed on the fastening portion 240 are a front coupling protrusion located in a front of the indentation surface where the engagement surface 231 of the coupling portion 230 is not formed, a left coupling protrusion located on a left side, and a right coupling protrusion located on a right side.

Here, a line connecting a surface where the left and right coupling protrusions face each other and a surface where the front coupling protrusion faces the indentation portion of the body part on a plane has a dovetail shape.

An internal angle between the surface where the left and right coupling protrusions face each other and the surface where the front coupling protrusion faces the indentation portion of the body part may be formed at an angle of 90 to 110°.

The coupling protrusion 250 has a cross section that may widen toward a bottom, and has a top thickness (t) of 0.5 to 5 mm.

In addition, a width of top and bottom of the coupling protrusion 250 may be formed in a ratio of 1:1.5 to 2.5., and the coupling protrusion 250 may be formed with trapezoidal cross sections or formed in a deformed trapezoid shape in which a hypotenuse is bent inward at an angle of 90 to 180°.

In order to achieve the above objective, according to another embodiment of the present disclosure, there is provided a bearing component 200 for an artificial knee joint including a body part 210, whose plane shape is oval as a whole, having an indentation portion 211 formed by depressing a part of the side surface of the body part to a predetermined depth toward a center of the body part 210, a protruding portion 220 formed on an upper surface of the body part 210 and introduced into an opening of a femoral component, a coupling portion 230 provided on a lower surface of the body part 210, and having an engagement surface 231 of a certain height to form a step difference with an outer circumferential surface of the body part, the engagement surface 231 being formed on the left and right sides of the coupling portion in a shape in which the shape of the body part is reduced by a predetermined ratio, and being not formed on an indentation surface up to a certain distance forward from the indentation portion 211 of the body part; and a fastening portion 240 having a coupling protrusion 250 that is continuous along a portion where the engagement surface 231 of the coupling portion 230 is not formed, and an air gap 242 formed in a space between the coupling protrusion and the coupling portion 230 along an outer surface of the coupling protrusion.

The bearing component 200 for an artificial knee joint according to another embodiment of the present disclosure is also made of at least one selected from the group consisting of a composite material comprising at least one from the group consisting of UHMWPE, PEEK, carbon fiber reinforced polymer or glass fiber reinforced polymer, and polyethylene (PE). Here, XLPE or HXLPE may be used as the UHMWPE and vitamin E may be further comprised in the UHMWPE.

A line connecting a surface facing the air gap 242 and a surface of the opposite coupling protrusion 250 on a plane has a dovetail shape. Here, an internal angle (β) between left and right surfaces of the coupling protrusion 250 and a surface facing the indentation portion of the body part may be formed at an angle of 90 to 110°.

The coupling protrusion 250 has a cross section that may widen toward a bottom, and has a top thickness of 0.5 to 5 mm.

Also, a width of top and bottom of the coupling protrusion 250 may be formed in a ratio of 1:1.5 to 2.5, and the coupling protrusion 250 may be formed with trapezoidal cross sections or formed in a deformed trapezoid shape in which a hypotenuse is bent inward at an angle of 90 to 180°.

The third embodiment of the present disclosure for achieving the above objective is an artificial knee joint including the bearing component 200 according to the first or second embodiment.

The artificial knee joint has the bearing component 200 that is inserted into a tibial component 300 along an inclination of a rim 360 of the tibial component 300, but as the bearing component 200 is positioned inside a front ridge of the tibial component 300 by a predetermined force, an accommodating portion 340 of the tibial component 300 comes into contact with a lower end of each coupling protrusion 250 at a constant height so that the bearing component 200 and the tibia component 300 are combined.

Here, the inclination of the rim 360 of the tibial component 300 may be formed by gradually lowering a height of the rim 360 from front to rear while forming an angle of 2 to 7° with the accommodating portion 340 of the tibial component 300.

The bearing component for an artificial knee joint of the present disclosure is configured to be elastically deformable when the coupling protrusions to be coupled to the outer perimeter of a dovetail-shaped protruding surface of a tibial component are coupled, so that engagement with the tibial component can be easy and maintained stably even after engagement.

Also, the impact force applied to a patient's bones during surgery can be minimized since the bearing component of the present disclosure requires less force when combined with the tibial component.

In addition, cost can be reduced since no special tools are required, and the risk associated with reoperation can be greatly reduced since the tibial component and the bearing component are easily separated from each other even with a small force thanks to elastically deformable coupling protrusions provided in the dovetail structure.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Hereinafter, preferred embodiments of the present disclosure will be described in detail with reference to the accompanying drawings. All terms and words used herein should not be construed as being limited to conventional or dictionary meanings but should be interpreted as meanings and concepts consistent with the technical spirit of the present disclosure.

Throughout the specification, when a member is referred to be located "on" another member, it should be understood that the member may be in contact with another member, but yet another member may exist in between. Throughout the specification, when a part "comprises" or "includes" a component, it means that other components may be further comprised or included, rather than excluding other components, unless otherwise stated.

Also, throughout the specification, when a component is referred to as being "connected" to another component, it should be understood that the component may be "directly connected" to another component, but the components may be "indirectly connected" with another member or element interposed therebetween.

Figure 6A:
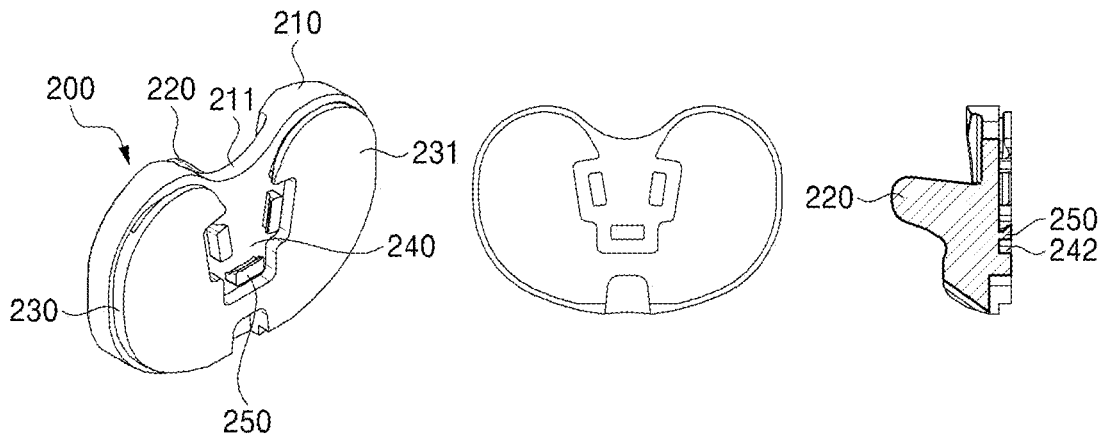
FIG. 6A is a perspective view, a front view, and a right side view showing a bearing component 200 according to the first embodiment of the present disclosure.
Figure 6B:
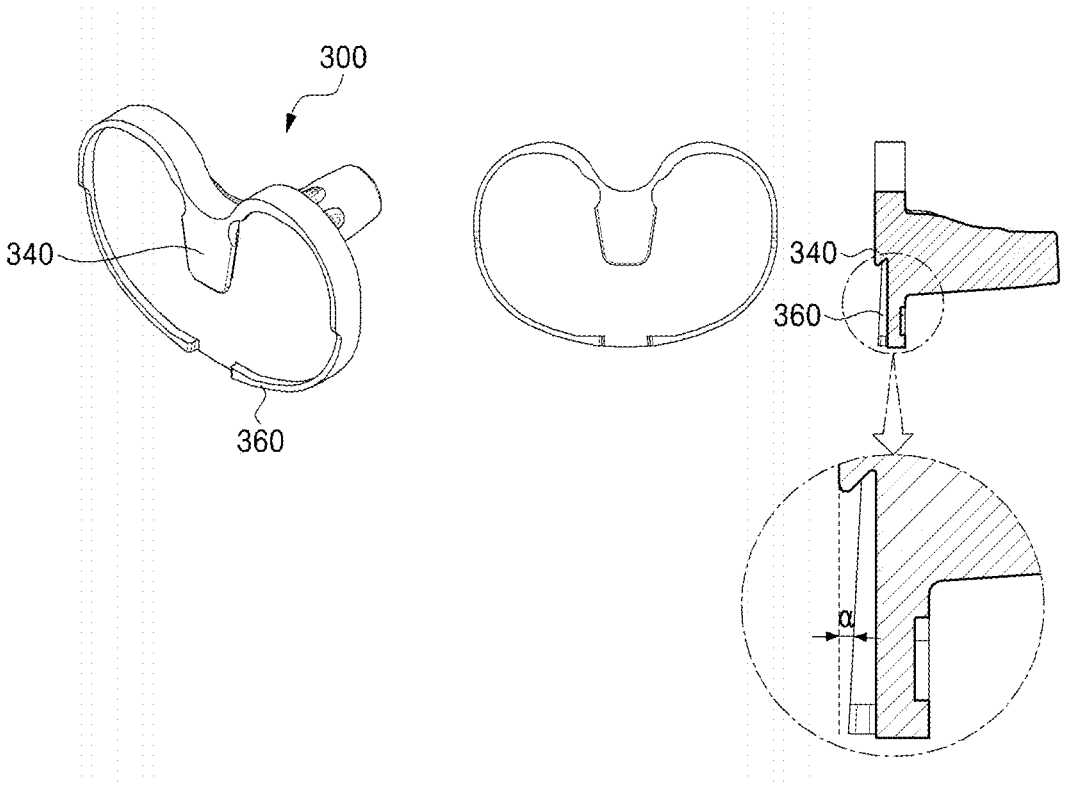
FIG. 6B is a perspective view, a front view, and a right side view showing a tibial component.
Figure 7:
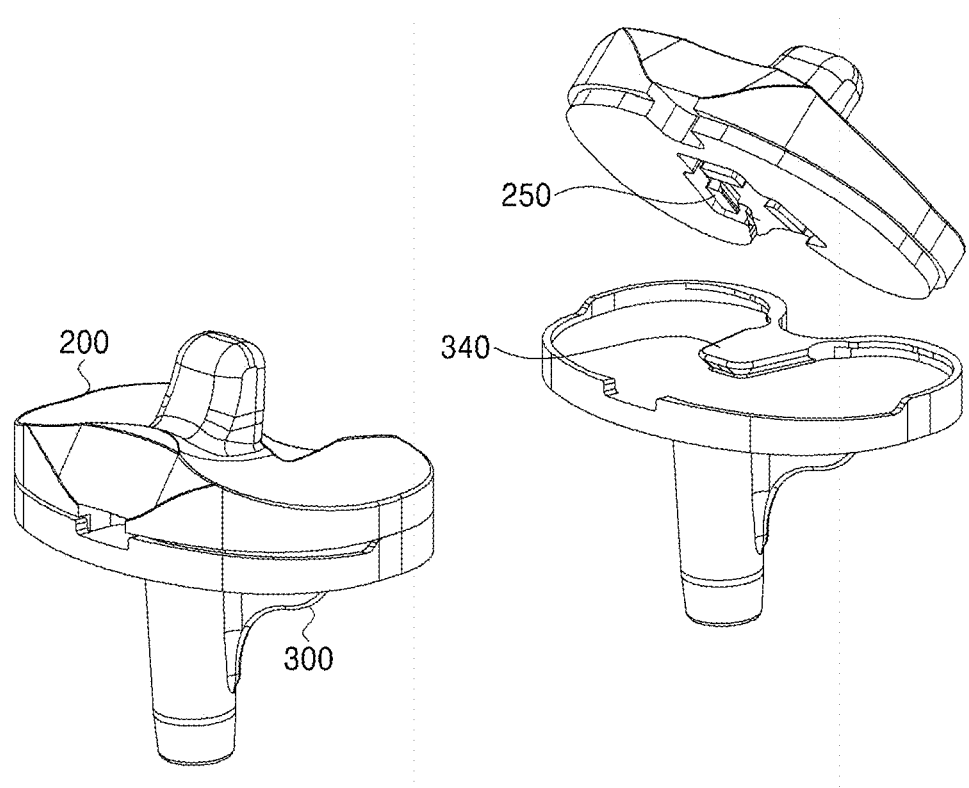
FIG. 7 is a view showing a state in which the bearing component 200 and the tibial component 300 according to the first embodiment of the present disclosure are coupled.

FIG. 6A is a perspective view, a front view, and a right side view showing a bearing component 200 according to the first embodiment of the present disclosure, and FIG. 6B is a perspective view, a front view, and a right side view showing a tibial component 300; and FIG. 7 is a view showing a coupled state and a pre-coupling state of the bearing component 200 and the tibial component 300.

Referring to these drawings, a bearing component 200 according to the first embodiment of the present disclosure may be composed of a body part 210, a protruding portion 220, a coupling portion 230, a fastening portion 240, and coupling protrusions 250.

The bearing component 200 serves as cartilage in the artificial knee joint and may be made of at least one selected from the group consisting of a composite material comprising at least one from the group consisting of UHMWPE (ultra high molecular weight polyethylene), PEEK (polyether, ether, ketone), carbon fiber reinforced polymer or glass fiber reinforced polymer, and polyethylene (PE).

Here, it is preferable that XLPE (crosslinked PE) or HXLPE (highly crosslinked PE) is used as the UHMWPE, and vitamin E may be further comprised in the UHMWPE. Vitamin E has antioxidant effects and is known to be effective in the treatment of arthritis, so it can reduce the possibility of inflammation after a knee replacement surgery.

The bearing component 200 made as described above has elasticity, so it is possible to stably couple with a tibial component 300 with only a small force, and even when separated, it is easy to separate with a small force, thereby minimizing damage to a patient's body caused by the impact force applied during surgery.

Referring to FIG. 6A, the body part 210 is oval as a whole and has an indentation portion 211 in which a posterior center is depressed to a predetermined depth toward a center of the body part to form the overall structure of the bearing component 200. Here, based on the appearance when the bearing component 200 and the tibial component 300 are combined and implanted in the body, the ventral direction of the body is anterior and the dorsal direction of the body is posterior.

On the upper surface of the body part 210, a protruding portion 220 formed by extending a predetermined length to be connected to a femoral component 11 (see FIG. 1 above) may be located. The protruding portion 220 may be formed in a tubular structure that increases in width toward the bottom and it is preferably formed in the center of the upper surface of the body part 210, but is not necessarily limited thereto.

When a person bends and straightens the knee, the femoral component 11 slides along the top surface of the bearing component 200 and the movement of the knee can be controlled, and here, the protruding portion 220 may be retracted into an opening (not shown) of the femoral component so that the femoral component 11 is not dislodged by the sliding movement.

Meanwhile, on the lower surface of the body part 210, a coupling portion 230, a fastening portion 240, and coupling protrusions 250 may be located.

The coupling portion 230 is configured to be coupled to the upper portion of the tibial component 300 in abutment. Referring to FIGS. 6 and 7, the coupling portion 230 is in surface contact with the tibial component 300 and serves to stably couple the bearing component 200 and the tibial component 300 to each other.

The coupling portion 230 has an engagement surface 231 of a certain height to form a step difference with an outer circumferential surface of the body part 210 on a lower surface of the body part 210, the engagement surface 231 being formed on the left and right sides of the coupling portion in a shape in which the shape of the body part is reduced by a predetermined ratio, and being not formed on an indentation surface up to a certain distance forward from the indentation portion 211 of the body part 210.

Referring to FIG. 6A, the fastening portion 240 may have a configuration in which a plurality of coupling protrusions 250 are formed near the center of the body part in a portion where the engagement surface 231 of the coupling portion 230 is not formed. The fastening portion 240 is preferably formed in a " ⊏ " shape on the left, right, and front three sides, respectively, as shown in FIG. 6 through processing using an end mill, but is not necessarily limited thereto.

Meanwhile, as confirmed in FIG. 6B, a rim 360 of the tibial component 300 has a portion of the front that may have a lower height than the rear, and is preferably formed to be inclined so that the height gradually decreases from the front to the rear along the rim 360.

Here, points at which the height of the rim 360 changes rapidly may be formed on the left and right sides of the coupling portion of the rim 360, and the positions of the points may be appropriately changed as needed in consideration of the coupling force or coupling convenience between the bearing component 200 and the tibial component 300. As an example, the points may be formed to be positioned at the center of the left side and at the center of the right side of the tibial component 300, respectively, or may be formed to be positioned in line with the center of the tibial component 300, but is not limited thereto.

Referring to the right side view of FIG. 6B, it is preferable that the rim 360 is formed by gradually lowering a height of the rim 360 from front to rear while forming an angle of 2 to 7° with the accommodating portion 340 of the tibial component 300. The angle range is considered so that an accommodating portion 340 of the tibial component 300 comes into contact with the bottom ends of the coupling protrusions 250 when the bearing component 200 is positioned inside a front ridge of the tibial component 300.

That is, as the bearing component 200 is inserted, by the inclination of the rim 360, the front of the accommodating portion 340 of the tibial component 300 comes into contact with the lower surface of the body part 210 where the engagement surface 231 of the coupling portion 230 is not formed, while coming into contact with the top ends of the coupling protrusions 250 first. Thereafter, when a certain force is applied to the bearing component 200 to be fixed into the front ridge of the tibial component 300, it is no longer affected by the inclined rim 360, thus the bearing component 200 and the tibial component 300 can be closely coupled as the accommodating portion 340 comes into contact with the bottom ends of the coupling protrusions 250 at a constant height.

When the angle is less than 2°, the effect of insertion through the inclination is insignificant and when the angle is greater than 7°, the accommodating portion 340 may not touch the top end of the front coupling protrusion located in the front of the fastening portion 240, therefore, if the angle is out of the above range, there is a disadvantage that an excessive force is still required to position the bearing component 200 inside the front ridge of the tibial component 300.

Figure 8:
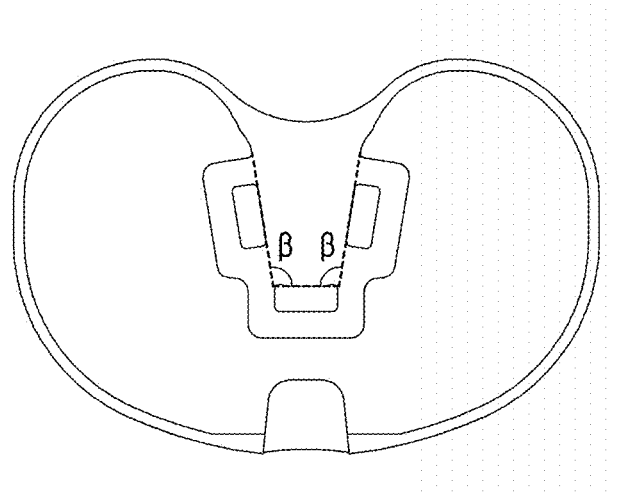
FIG. 8 is a view showing a relationship between coupling protrusions formed on an engagement surface of the bearing component 200 of the present disclosure and an outer perimeter (dotted line) of a dovetail-shaped protruding surface of the tibial component 300.

FIG. 8 is a view showing a relationship between coupling protrusions 250 formed on an engagement surface of the bearing component 200 according to the first embodiment of the present disclosure and an outer perimeter (dotted line) of a dovetail-shaped protruding surface (accommodating portion, 340) of a tibial component 300.

Referring to FIG. 8, a plurality of coupling protrusions 250 formed in the fastening portion 240 are a front coupling protrusion located in a front of the indentation surface where the engagement surface 231 of the coupling portion 230 is not formed, a left coupling protrusion located on a left side, and a right coupling protrusion located on a right side.

The coupling protrusions 250 serve to maintain a stable coupling between the bearing component 200 and the tibial component 300, especially playing a role in helping the coupling of the rear side to be strong. In addition, when the bearing component 200 is separated from the tibial component 300, it can be easily and quickly separated with a small force thanks to the elasticity of the coupling protrusions 250.

Here, in the case of the bearing component 200 according to the first embodiment of the present disclosure, a line connecting a surface where the left and right coupling protrusions face each other and a surface where the front coupling protrusion faces the indentation portion of the body part on a plane has a dovetail shape.

It is preferable that an internal angle between the surface where the left and right coupling protrusions face each other and the surface where the front coupling protrusion faces the indentation portion of the body part be formed at an angle of 90 to 110°. If the angle is out of that range, the surface area where the coupling protrusions 250 and the accommodating portion 340 abut is reduced, thereby reducing the engagement force between the bearing component 200 and the tibial component 300.

Figure 9:
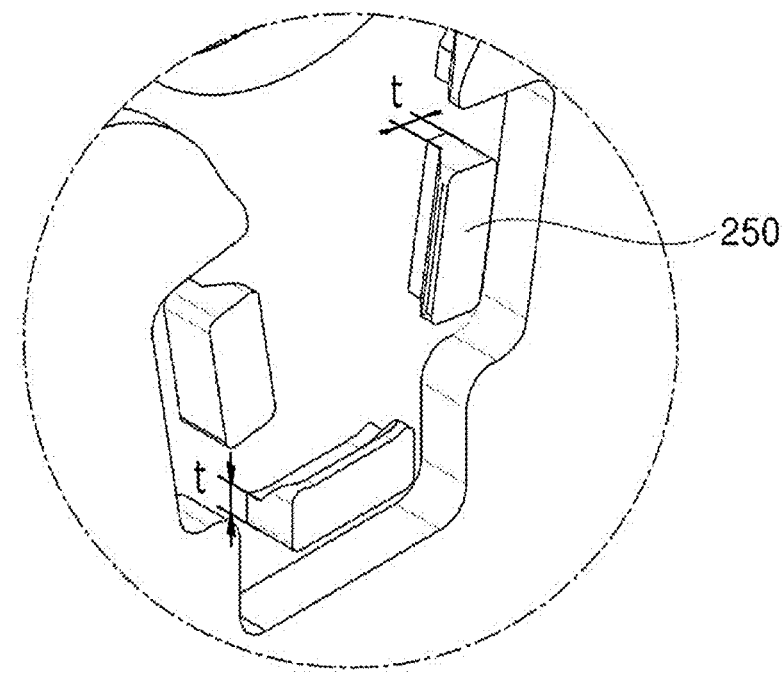
FIG. 9 is an enlarged perspective view of the coupling protrusions formed on the bearing component 200 according to the first embodiment of the present disclosure.

FIG. 9 is an enlarged perspective view of the coupling protrusions formed on the bearing component 200 according to the first embodiment of the present disclosure.

Figure 3A:
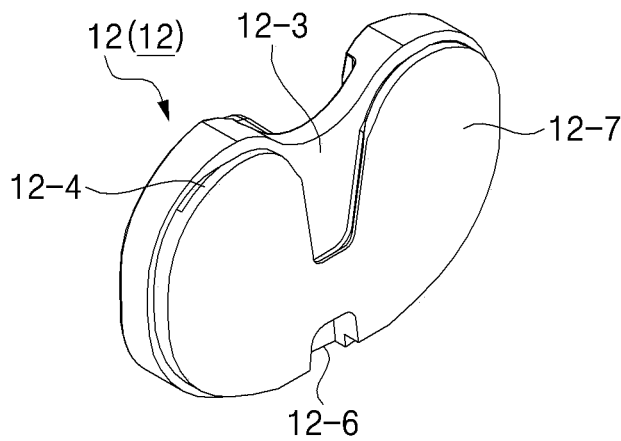
FIGS. 3A-3B are views showing the configuration of a locking mechanism for fixing a bearing component 12 to a tibial component 13 in a dovetail type of the conventional art.
Figure 3B:
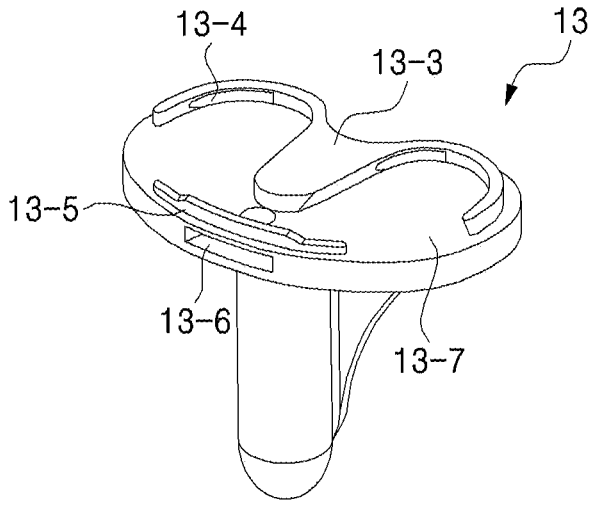
Figure 4A:
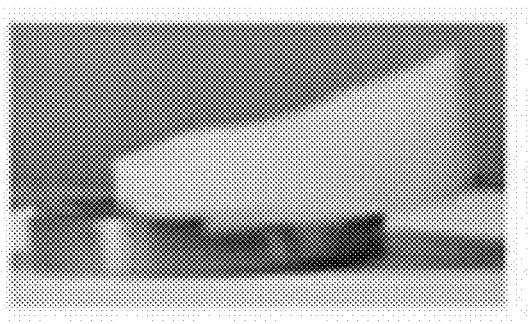
FIGS. 4A-4E are views showing a process of fastening the bearing component 12 to the tibial component in the dovetail type of the conventional art.
Figure 4B:
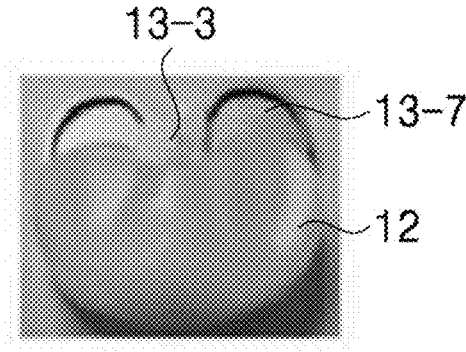
Figure 4C:
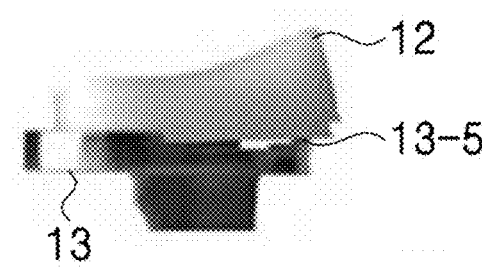
Figure 4D:
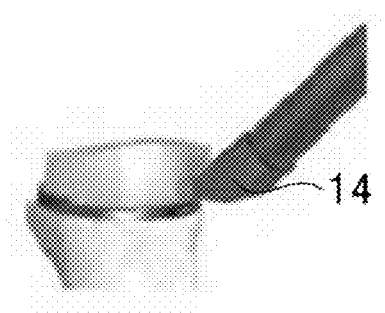
Figure 4E:
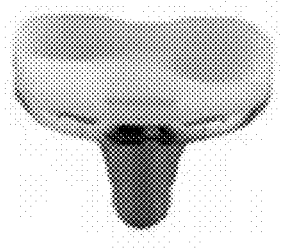
Figure 5A:
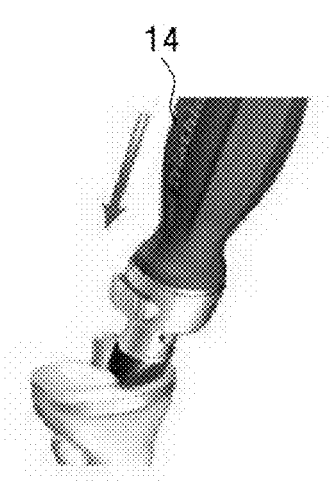
FIGS. 5A-5B are views showing tools necessary for the process of fastening the bearing component 12 to the tibial component in the dovetail type of the conventional art.
Figure 5B:
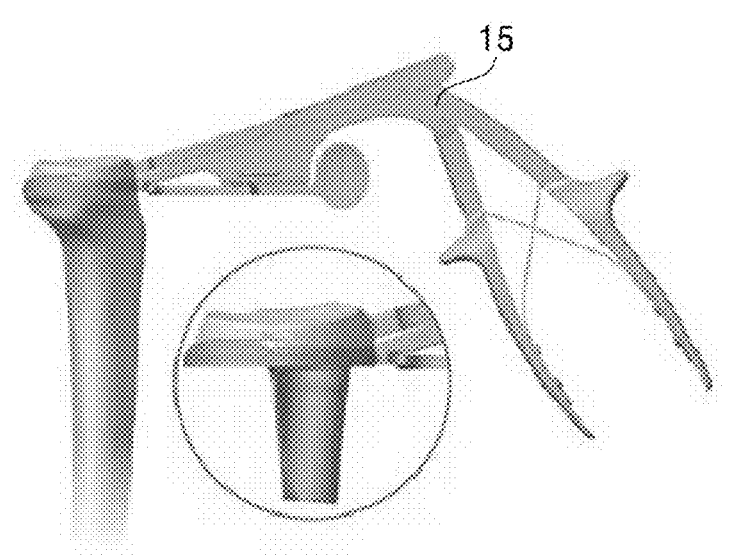

As can be seen in FIGS. 3 and 4, the bearing component 12 according to the conventional art is engaged with the tibial component by being inserted into the tibial component in surface contact, so that an excessive force was required to be engaged or disengaged. On the contrary, the bearing component 200 of the first embodiment can be stably coupled to or easily separated from the tibial component 300 with only a small force thanks to the coupling protrusions 250 having elasticity.

Referring to the right side view of FIG. 6 and FIG. 9, the coupling protrusion 250 has a cross section that widens toward a bottom. Also, it is preferable that the cross section to have a trapezoidal or "ㄱ" shape, but is not necessarily limited thereto, and it can be transformed into various shapes as needed. For example, the cross section may be formed in a trapezoidal shape, but the upper and lower bases may not be parallel to each other, or as seen in the right side view of FIG. 6 and FIG. 9, a portion of the hypotenuse may be deformed into a shape bent inward at a predetermined angle.

Here, it is preferable that the portion of the hypotenuse be bent at an angle of about 90 to 180°, and more preferably, it may be formed at an angle of about 130 to 140°. Here, if the angle is less than 90°, when the bearing component 200 is inserted, the bottom ends of the coupling protrusions 250 may first contact the accommodating portion 340 of the tibial component 300 and be bent, thereafter, the coupling protrusions 250 may be bent and separated by the applied force, and thus, in the case of separating the coupled bearing component 200, there is a disadvantage that the coupling protrusions 250 cannot be used as a means of elastic retraction.

On the other hand, if the angle is greater than 180°, the bottom ends of the coupling protrusions 250 may not contact the accommodating portion 340, making them unable to fasten the accommodating portion 340.

In addition, the coupling protrusion 250 may be formed one each on the left and right sides of the fastening portion 240 and in the front of the indentation surface where the engagement surface 231 of the coupling portion 230 is not formed, and it is preferable to be spaced apart from the engagement surface by a predetermined distance, but the number and spacing of the coupling protrusions are not necessarily limited thereto.

It is preferable that the coupling protrusion 250 have a top thickness of 0.5 to 5 mm, and more preferably, a thickness of 1.5 mm. When the coupling protrusion 250 has a top thickness of less than 0.5 mm, the coupling protrusion 250 may be separated from the body part 210, thereby reducing the engagement force between the bearing component 200 and the tibial component 300.

On the other hand, when the coupling protrusion 250 has a top thickness of greater than 5 mm, the coupling protrusion 250 does not retract when the bearing component 200 is inserted since the coupling protrusion 250 does not have elasticity, which makes it difficult to engage with the tibial component 300.

It is preferable that a width of top and bottom of the coupling protrusion 250 be formed in a ratio of 1:1.5 to 2.5. When the ratio is less than 1.5, the surface area in which the bottom end of the coupling protrusion 250 comes into contact with the bottom end of the accommodating portion 340 is reduced, thus the engagement force may be reduced. When the ratio is greater than 2.5, the manufacturing process is inefficient and uneconomical while the effect of increasing the engagement force is insignificant.

Figure 10:
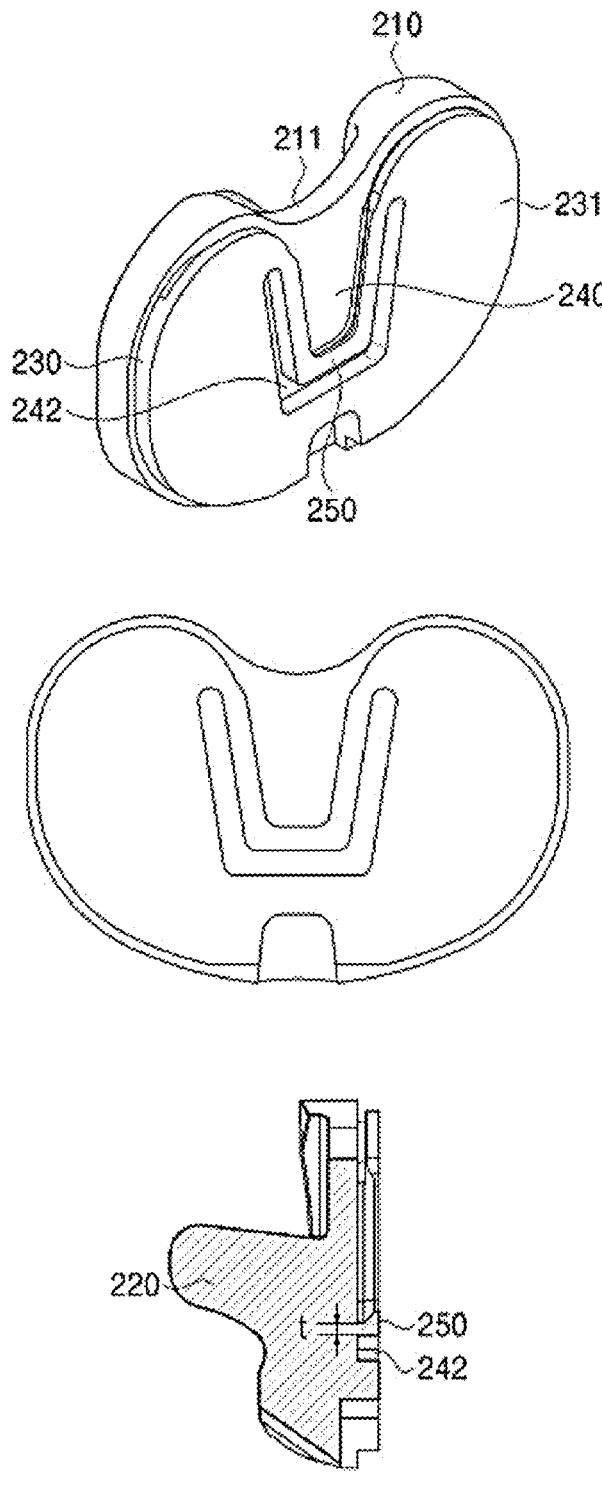
FIG. 10 is a perspective view, a front view, and a right side view showing a bearing component 200 according to the second embodiment of the present disclosure.

FIG. 10 is a perspective view, a front view, and a right side view showing a bearing component 200 according to the second embodiment of the present disclosure. In the description of the present second embodiment, the same configuration as the bearing component 200 of the above-described first embodiment will be described by assigning the same reference numerals.

Referring to FIG. 10, the bearing component 200 according to the second embodiment may also include a body part 210, a protruding portion 220, a coupling portion 230, a fastening portion 240, and a coupling protrusion 250.

The bearing component 200 serves as cartilage in the artificial knee joint and may be made of at least one selected from the group consisting of a composite material comprising at least one from the group consisting of UHMWPE (ultra high molecular weight polyethylene), PEEK (polyether, ether, ketone), carbon fiber reinforced polymer or glass fiber reinforced polymer, and polyethylene (PE).

Here, it is preferable that XLPE (crosslinked PE) or HXLPE (highly crosslinked PE) is used as the UHMWPE, and vitamin E may be further comprised in the UHMWPE. Vitamin E has antioxidant effects and is known to be effective in the treatment of arthritis, so it can reduce the possibility of inflammation after a knee replacement surgery.

The bearing component 200 made as described above has elasticity, so it is possible to stably couple with a tibial component (300, see FIG. 7 above) with only a small force, and even when separated, it is easy to separate with a small force, thereby minimizing damage to a patient's body caused by the impact force applied during surgery.

The body part 210 is oval as a whole and has an indentation portion 211 in which a posterior center is depressed to a predetermined depth toward a center of the body part to form the overall structure of the bearing component 200. Here, based on the appearance when the bearing component 200 and the tibial component 300 are combined and implanted in the body, the ventral direction of the body is anterior and the dorsal direction of the body is posterior.

Figure 1A:
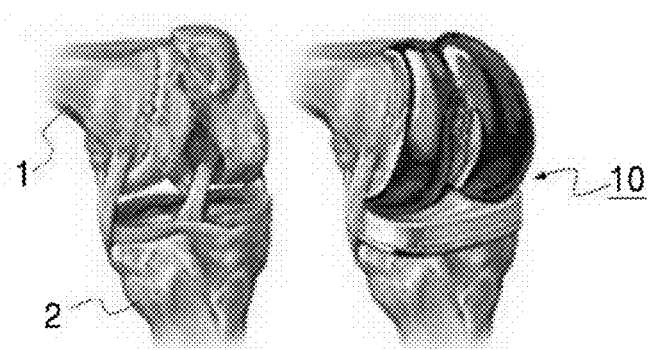
FIG. 1A is a view showing a knee of a patient before and after a knee replacement surgery is performed.
Figure 1B:
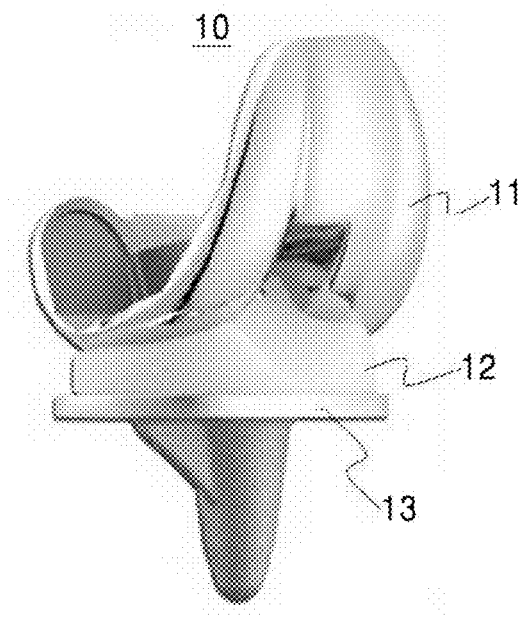
FIG. 1B is a view showing an artificial knee joint 10 according to the conventional art.
Figure 2:
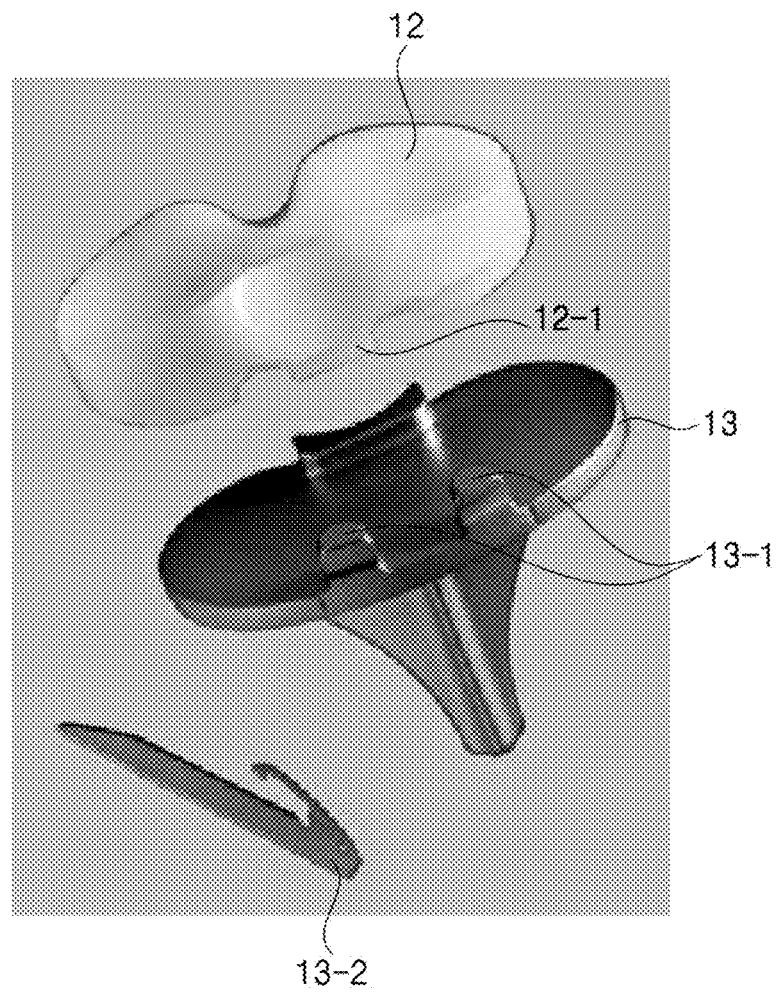
FIG. 2 is a view showing the configuration of a locking mechanism for fixing a bearing component 12 to a tibial component 13 in a pin type of the conventional art.

On the upper surface of the body part 210, a protruding portion 220 formed by extending a predetermined length to be connected to a femoral component (11, see FIG. 1 above)

may be located. The protruding portion 220 may be formed in a tubular structure that increases in width toward the bottom and it is preferably formed in the center of the upper surface of the body part 210, but is not necessarily limited thereto.

When a person bends and straightens the knee, the femoral component 11 slides along the top surface of the bearing component 200 and the movement of the knee can be controlled, and here, the protruding portion 220 may be retracted into an opening (not shown) of the femoral component so that the femoral component 11 is not dislodged by the sliding movement.

Meanwhile, on the lower surface of the body part 210, a coupling portion 230, a fastening portion 240, and a coupling protrusion 250 may be located.

The coupling portion 230 is configured to be coupled to the upper portion of the tibial component 300 in abutment, and is in surface contact with the tibial component 300, serving to stably couple the bearing component 200 and the tibial component 300 (see FIG. 7 above) to each other.

The coupling portion 230 has an engagement surface 231 of a certain height to form a step difference with an outer circumferential surface of the body part 210 on a lower surface of the body part 210, the engagement surface 231 being formed on the left and right sides of the coupling portion in a shape in which the shape of the body part is reduced by a predetermined ratio, and being not formed on an indentation surface up to a certain distance forward from the indentation portion 211 of the body part 210.

As shown in FIG. 10, the fastening portion 240 includes a coupling protrusion 250 that is continuous along a portion where the engagement surface 231 of the coupling portion 230 is not formed, and an air gap 242 formed in a space between the coupling protrusion and the coupling portion 230 along an outer surface of the coupling protrusion so that when an accommodating portion 340 of the tibial component 300 is coupled, the air gap provides a free space in which the coupling protrusion 250 may be retracted.

Here, the fastening portion 240 is preferably formed in a "⊏" shape on the left, right, and front three sides, respectively, as shown in FIG. 10 through processing using an end mill, but is not necessarily limited thereto.

Figure 11:
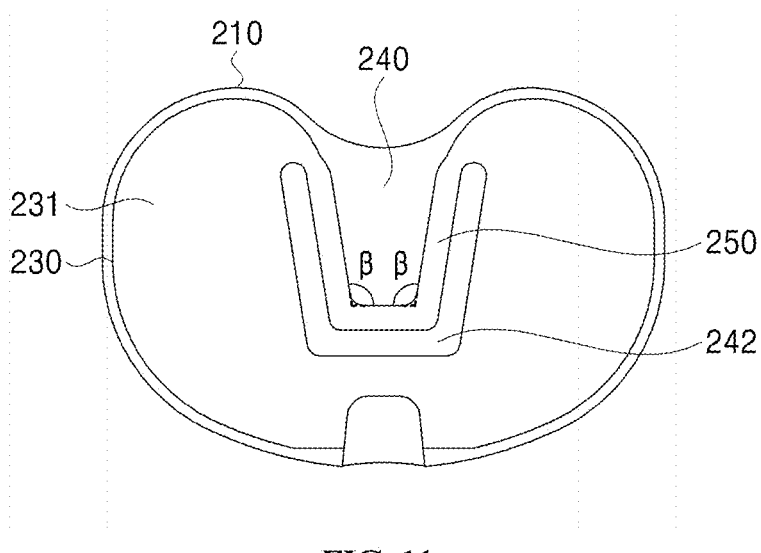
FIG. 11 is a view showing a relationship between a coupling protrusion 250 formed on an engagement surface of the bearing component 200 and an outer perimeter (dotted line) of a dovetail-shaped protruding surface (accommodating portion, 340) of a tibial component 300 according to the second embodiment of the present disclosure.

FIG. 11 is a view showing a relationship between a coupling protrusion 250 formed on an engagement surface of the bearing component 200 and an outer perimeter (dotted line) of a dovetail-shaped protruding surface (accommodating portion, 340) of a tibial component 300 according to the second embodiment of the present disclosure.

Referring to FIG. 11, a coupling protrusion 250, which was a plurality in the first embodiment, formed on the fastening portion 240 is configured in a continuous form along a portion where the coupling protrusion is not formed. The air gap 242 having a substantially dovetail concave (凹) shape is formed between the continuously formed coupling protrusion and the coupling part 230 along the outer surface of the coupling protrusion 250.

The coupling protrusion 250 serves to maintain a stable coupling between the bearing component 200 and the tibial component 300, especially playing a role in helping the coupling of the rear side to be strong. In addition, when the bearing component 200 is separated from the tibial component 300, it can be easily and quickly separated with a small force thanks to the elasticity of the coupling protrusion 250.

In the case of the bearing component 200 according to the second embodiment of the present disclosure, a line connecting a surface facing the air gap 242 and a surface of the opposite coupling protrusion 250 on a plane has a dovetail shape.

Here, it is preferable that an internal angle between a surface of the left and right side of the coupling protrusion and a surface facing an indentation portion of the body part is formed at an angle of 90 to 110°. If the angle is out of that range, the surface area where the coupling protrusion 250 and the accommodating portion 340 abut is reduced, thereby reducing the engagement force between the bearing component 200 and the tibial component 300.

Figure 12:
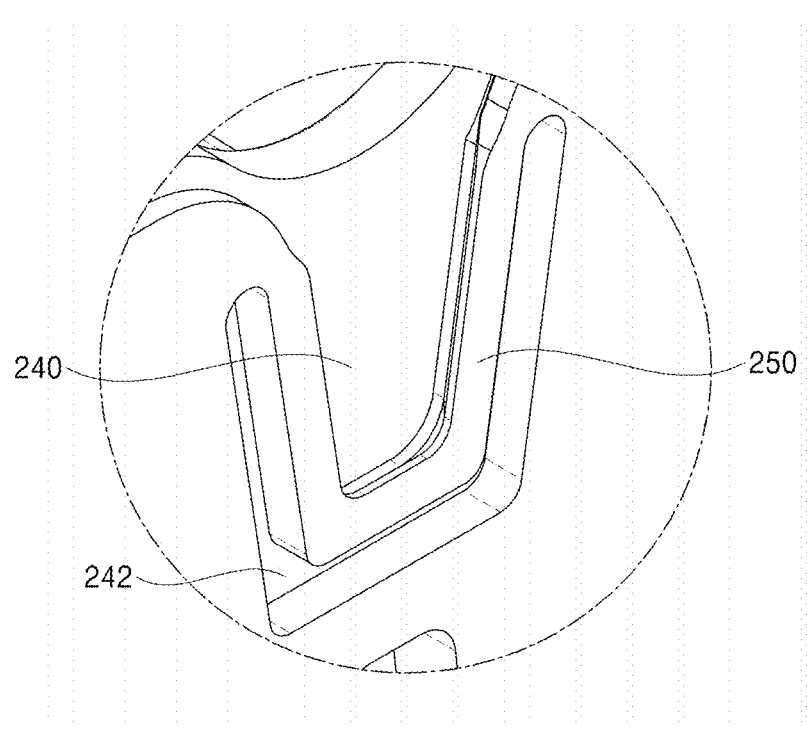
FIG. 12 is an enlarged perspective view of a coupling protrusion formed on the bearing component 200 shown in FIG. 10.

Meanwhile, FIG. 12 is an enlarged perspective view of a coupling protrusion 250 formed on the bearing component 200 of the second embodiment.

As can be seen in FIGS. 3 and 4, the bearing component 12 according to the conventional art is engaged with the tibial component by being inserted into tibial component in surface contact, so that an excessive force was required to be engaged or disengaged. On the contrary, the bearing component 200 according to the second embodiment can be stably coupled to or easily separated from the tibial component 300 with only a small force thanks to the coupling protrusion 250 having elasticity.

Referring to the right side view of FIG. 10 and FIG. 12, the coupling protrusion 250 has a cross section that widens toward a bottom. Also, it is preferable that the cross section to have a trapezoidal or "⌐" shape, but is not necessarily limited thereto, and it can be transformed into various shapes as needed. For example, the cross section may be formed in a trapezoidal shape, but the upper and lower bases may not be parallel to each other, or as seen in the right side view of FIG. 10 and FIG. 12, a portion of the hypotenuse may be deformed into a shape bent inward at a predetermined angle.

Here, it is preferable that the portion of the hypotenuse be bent at an angle of about 90 to 180°, and more preferably, it may be formed at an angle of about 130 to 140°. Here, when the angle is less than 90°, when the bearing component 200 is inserted, the bottom ends of the coupling protrusions 250 may first contact the accommodating portion 340 of the tibial component 300 and be bent, thereafter, the coupling protrusions 250 may be bent and separated by the applied force, and thus, in the case of separating the coupled bearing component 200, there is a disadvantage that the coupling protrusions 250 cannot be used as a means of elastic retraction.

On the other hand, when the angle is greater than 180°, the bottom ends of the coupling protrusions 250 may not contact the accommodating portion 340, making them unable to fasten the accommodating portion 340.

In addition, the coupling protrusion 250 may be formed continuously along the left and right sides of the fastening portion 240 and the front of the indentation surface where the engagement surface 231 of the coupling portion 230 is not formed, and it is preferable to be spaced apart from the engagement surface by a predetermined distance.

It is preferable that the coupling protrusion 250 have a top thickness of 0.5 to 5 mm, and more preferably, a thickness of 1.5 mm. When the coupling protrusion 250 has a top thickness of less than 0.5 mm, the coupling protrusion 250 may be separated from the body part 210, thereby reducing the engagement force between the bearing component 200 and the tibial component 300.

On the other hand, when the coupling protrusion 250 has a top thickness of greater than 5 mm, the coupling protrusion 250 does not retract when the bearing component 200 is inserted since the coupling protrusion 250 does not have elasticity, which makes it difficult to engage with the tibial component 300.

It is preferable that a width of top and bottom of the coupling protrusion 250 be formed in a ratio of 1:1.5 to 2.5. When the ratio is less than 1.5, the surface area in which the bottom end of the coupling protrusion 250 comes into contact with the bottom end of the accommodating portion 340 is reduced, thus the engagement force may be reduced. When the ratio is greater than 2.5, the manufacturing process is inefficient and uneconomical while the effect of increasing the engagement force is insignificant.

In the above detailed description of the present disclosure, only specific embodiments thereof have been described. It should be understood, however, that the present disclosure is not limited to the particular forms mentioned in the detailed description, but rather, covers all modifications and equivalents and substitutions falling within the spirit and scope of the disclosure as defined by the appended claims.

That is, the present disclosure is not limited to the specific embodiments and descriptions described above, and various modifications can be made by anyone skilled in the art without departing from the gist of the present disclosure as claimed in the claims, and all such modifications are within the protection scope of the present disclosure.

What is claimed is:

1. A bearing component (200) for an artificial knee joint, the bearing component comprising:

a body part (210) having a plane shape that is oval as a whole, having an indentation portion (211) formed by depressing a part of a rear side of the body part to a predetermined depth toward a center of the body part;

a protruding portion (220) protruding from a top side of the body part (210) to a predetermined height and configured to be introduced into an opening of a femoral component;

a coupling portion (230) provided on a bottom surface of the body part (210) opposite to the protruding portion (220), and including:

a plurality of coupling protrusions (250) formed on a central portion of the bottom surface of the body part, wherein the central portion of the bottom surface of the body part includes the center of the body part, and wherein the plurality of coupling protrusions (250) includes a front coupling protrusion disposed at a position forward of the center of the body part, a left coupling protrusion disposed to the left of the front coupling protrusion and at a position rearward of the center of the body part, and a right coupling protrusion disposed to the right of the front coupling protrusion and at a position rearward of the center of the body part, wherein the front coupling protrusion, the left coupling protrusion, and the right coupling protrusion are spaced apart from each other, wherein each of the front, left, and right coupling protrusions has a bottom thickness greater than a top thickness, such that a groove is formed at a top portion of each protrusion, and wherein the grooves of the left and right coupling protrusions are open to face each other, and the groove of the front coupling protrusion is open to face the indentation portion (211); and an engagement surface (231) having a plate shape as a whole with a predetermined height to form a step difference from the bottom surface of the body part, the engagement surface (231) being formed on left, front, and right sides on the bottom surface of the body part and being not formed on the central portion and near the indentation portion (211) of the bottom surface of the body part such that the engagement surface (231) surrounds the plurality of coupling protrusions (250), wherein the coupling portion (230) provides a dovetail type locking mechanism formed by the grooves of the left, front, and right coupling protrusions, having a truncated cone or ⨆ shape that gradually widens toward the indentation portion, wherein the dovetail type locking mechanism of the coupling portion (230) is configured to be engaged with an accommodating portion (340) of a tibial component (300).

2. A bearing component (200) for an artificial knee joint, the bearing component comprising:

a body part (210) having a plane shape that is oval as a whole, having an indentation portion (211) formed by depressing a part of a rear side of the body part to a predetermined depth toward a center of the body part;

a protruding portion (220) protruding from a top side of the body part (210) to a predetermined height and configured to be introduced into an opening of a femoral component;

a coupling portion (230) provided on a bottom surface of the body part (210) opposite to the protruding portion (220), and including:

a coupling protrusion (250) formed on a central portion of the bottom surface of the body part, wherein the central portion of the bottom surface of the body part includes the center of the body part, and wherein the coupling protrusion (250) includes a front part disposed at a position forward of the center of the body part, a left part extending from the left end of the front part toward the indentation portion of the body part, wherein a portion of the left part is disposed at a position rearward of the center of the body part, and a right part extending from the right end of the front part toward the indentation portion of the body part, wherein a portion of the right part is disposed at a position rearward of the center of the body part, wherein each of the front, left, and right parts of the coupling protrusion (250) has a bottom thickness greater than a top thickness, such that a groove is formed at a top portion of each part, wherein the grooves of the left and right parts are open to face each other, and the groove of the front part is open to face the indentation portion (211); and an engagement surface (231) having a plate shape as a whole with a predetermined height to form a step difference from the bottom surface of the body part, the engagement surface (231) being formed on left, front, and right sides on the bottom surface of the body part and being not formed on the central portion and near the indentation portion (211) of the bottom surface of the body part such that the engagement surface (231) surrounds the coupling protrusion (250), wherein the coupling portion (230) provides a dovetail type locking mechanism formed by the grooves of the left, front, and right parts, having a truncated cone or ⊔ shape that gradually widens toward the indentation portion, and an air gap (242) is formed between the coupling protrusion and the engagement surface (231) along outer surfaces of the coupling protrusion such that where an accommodating portion (340) of a tibial component (300) is engaged, the air gap provides a free space in which the coupling protrusion (250) is configured to be retracted.

3. The bearing component (200) of claim 1, wherein an internal angle (β) between surfaces of the left and right coupling protrusions that face each other and a surface of the front coupling protrusion facing the indentation portion of the body part is formed at an angle of 90 to 110°.

4. The bearing component (200) of claim 2, wherein an internal angle (β) between the inner surfaces of the left and right parts of the coupling protrusion (250) and the inner surface of the front part of the coupling protrusion facing the indentation portion of the body part is formed at an angle of 90 to 110°.

5. The bearing component (200) of claim 1, wherein each of the plurality of coupling protrusions (250) has a cross section that widens toward a bottom.

6. The bearing component (200) of claim 1, wherein the top thickness of each of the plurality of coupling protrusions (250) is 0.5 to 5 mm.

7. The bearing component (200) of claim 1, wherein the top and bottom thicknesses of each of the plurality of coupling protrusions (250) are formed in a ratio of 1:1.5 to 2.5.

8. The bearing component (200) of claim 1, wherein each of the plurality of coupling protrusions (250) is formed with trapezoidal cross sections or formed in a deformed trapezoid shape in which a hypotenuse is bent inward at an angle of 90 to 180°.

9. The bearing component (200) of claim 2, wherein the coupling protrusion (250) has a cross section that widens toward a bottom.

10. The bearing component (200) of claim 2, wherein the top thickness of the coupling protrusion (250) is 0.5 to 5 mm.

11. The bearing component (200) of claim 2, wherein the top and bottom thicknesses of the coupling protrusion (250) are formed in a ratio of 1:1.5 to 2.5.

12. The bearing component (200) of claim 2, wherein the coupling protrusion (250) is formed with trapezoidal cross sections or formed in a deformed trapezoid shape in which a hypotenuse is bent inward at an angle of 90 to 180°.

13. An artificial knee joint comprising:
the bearing component (200) of claim 1; and
the tibial component (300) comprising:
a rim (360) having an inclination,
the accommodating portion (340) provided on a top surface of the tibial component,
wherein the bearing component (200) is inserted along the inclination of the rim (360) of the tibial component (300) whereby the accommodating portion (340) of the tibial component (300) closely comes into contact with a lower end of each coupling protrusion (250).

14. The artificial knee joint of claim 13, wherein the inclination of the rim (360) of the tibial component (300) is formed such that a height of the rim (360) gradually lowers from a front side to a rear side of the tibial component (300) while forming an angle of 2 to 7° with the accommodating portion (340) of the tibial component (300).

15. An artificial knee joint comprising:
the bearing component (200) of claim 2; and
the tibial component (300) comprising:
a rim (360) having an inclination,
the accommodating portion (340) provided on a top surface of the tibial component,
wherein the bearing component (200) is inserted along the inclination of the rim (360) of the tibial component (300) whereby the accommodating portion (340) of the tibial component (300) closely comes into contact with a lower end of the coupling protrusion (250).

16. The artificial knee joint of claim 15, wherein the inclination of the rim (360) of the tibial component (300) is formed such that a height of the rim (360) gradually lowers from a front side to a rear side of the tibial component (300) while forming an angle of 2 to 7° with the accommodating portion (340) of the tibial component (300).

* * * * *